US008063259B2

(12) United States Patent
Butler et al.

(10) Patent No.: US 8,063,259 B2
(45) Date of Patent: *Nov. 22, 2011

(54) TOLUENE DISPROPORTIONATION USING NB/MORDENITE CATALYST

(75) Inventors: James R. Butler, League City, TX (US); Rosa Hall, Houston, TX (US); Xin Xiao, Augusta, GA (US)

(73) Assignee: Fina Technology, Inc., Houston, TX (US)

( * ) Notice: Subject to any disclaimer, the term of this patent is extended or adjusted under 35 U.S.C. 154(b) by 521 days.

This patent is subject to a terminal disclaimer.

(21) Appl. No.: 12/193,685

(22) Filed: Aug. 18, 2008

(65) Prior Publication Data

US 2010/0041934 A1   Feb. 18, 2010

(51) Int. Cl.
 *C07C 6/12* (2006.01)
(52) U.S. Cl. ...................................................... 585/475
(58) Field of Classification Search .................. 585/475
 See application file for complete search history.

(56) References Cited

U.S. PATENT DOCUMENTS

| | | |
|---|---|---|
| 3,436,174 A | 4/1969 | Sand |
| 3,480,539 A | 11/1969 | Voorhies et al. |
| 3,819,736 A | 6/1974 | Sato et al. |
| 4,347,395 A | 8/1982 | Chu et al. |
| 4,371,457 A | 2/1983 | Chu |
| 4,469,909 A | 9/1984 | Chester et al. |
| 4,956,511 A | 9/1990 | Butler et al. |
| 5,336,824 A | 8/1994 | Shamshoum et al. |
| 6,462,247 B1 | 10/2002 | Kelly et al. |
| 6,504,076 B1 | 1/2003 | Xiao et al. |
| 6,803,493 B1 | 10/2004 | Xiao et al. |
| 6,846,964 B2 | 1/2005 | Xiao et al. |
| 7,241,911 B2 | 7/2007 | Beck et al. |
| 7,378,365 B2 | 5/2008 | Boldingh et al. |
| 7,439,204 B2 | 10/2008 | McMinn et al. |
| 2008/0319243 A1 | 12/2008 | Butler et al. |

*Primary Examiner* — Thuan Dinh Dang (57) ABSTRACT

A molecular sieve catalyst useful in the conversion of hydrocarbons containing niobium is disclosed, along with a process for the disproportionation of toluene to benzene and xylene using such catalyst.

14 Claims, 5 Drawing Sheets

TOLUENE DISPROPORTIONATION USING NB/MORDENITE CATALYST

CROSS-REFERENCE TO RELATED APPLICATIONS

Not applicable.

FIELD

This invention relates to the disproportionation of alkylaromatic feedstreams.

BACKGROUND

The disproportionation of toluene involves a well known transalkylation reaction in which toluene is converted to benzene and xylene, often referred to as a Toluene Disproportionation Process or TDP, in accordance with the following reaction:

Toluene Disproportionation: Toluene⟵⟶Benzene+Xylene    (1)

Mordenite is one of a number of molecular sieve catalysts useful in the transalkylation of alkylaromatic compounds. Mordenite is a crystalline aluminosilicate zeolite exhibiting a network of silicon and aluminum atoms interlinked by oxygen atoms within the crystalline structure. For a general description of mordenite catalysts, reference is made to Kirk-Othmer, Encyclopedia of Chemical Technology, 3rd Edition, 1981, under the heading "Molecular Sieves", Vol. 15, pages 638-643, which is incorporated by reference herein. Mordenite, as found in nature or as synthesized to replicate the naturally occurring zeolite, typically exhibits a relatively low silica-to-alumina mole ratio of about 10 or less. Also known, however, are mordenite catalysts exhibiting substantially lower alumina content. These alumina deficient mordenite catalysts exhibit silica-to-alumina ratios greater than 10, ranging up to about 100, and may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies et al, both of which are incorporated by reference herein. Both the typical and the aluminum deficient mordenites are known to be useful in the disproportionation of toluene.

Disproportionation of toluene feedstock may be performed at temperatures ranging from 200° C. to 600° C. or above and at pressures ranging from atmospheric to 100 atmospheres or above and at liquid hourly space velocities (LHSV) of around 1 to 10 hr$^{-1}$. The specific catalyst, however, may impose constraints on reaction temperatures in terms of catalyst activity and aging characteristics. In general relatively high temperatures are used when employing the high aluminum mordenites (low silica-to-alumina ratios) and somewhat lower temperatures when employing the low alumina mordenites. Accordingly, where mordenite catalysts exhibiting high silica/alumina ratios have been employed in the transalkylation of alkylaromatics, it has been the practice to operate toward the lower end of the temperature range.

Hydrogen is generally supplied along with toluene to the reaction zone. While the disproportionation reaction (1) does not involve chemical consumption of hydrogen, the use of a hydrogen co-feed is generally considered to prolong the useful life of the catalyst. The amount of hydrogen supplied, which normally is measured in terms of the hydrogen/toluene mole ratio, is generally shown in the prior art to increase as temperature increases. The hydrogen:toluene mole ratio can generally range from 0.05:1 to 5:1.

Nickel-Mordenite TDP catalysts can have good activity and selectivity, but at times produce more non-aromatic compounds than desired. In view of the above, it would be desirable to have a process of conducting toluene disproportionation with a mordenite catalyst with lower production of non-aromatic compounds.

SUMMARY

An embodiment of the present invention is a molecular sieve catalyst containing niobium useful in the conversion of hydrocarbons. The niobium content can be at least 0.05 wt %. The molecular sieve catalyst can be a zeolite, and can be a mordenite zeolite. The catalyst can be used in a toluene disproportionation reaction process and can provide a toluene conversion at a rate of at least 30 wt % and non-aromatic selectivity of less than 1.0 wt %. The toluene disproportionation reaction process can continue with a toluene conversion of at least 30 percent for at least 30 days with an average catalyst deactivation no more than 1.0° C./day. The toluene disproportionation reaction process can provide a toluene conversion of at least 30 wt % with a methylcyclopentane content of less than 0.005 wt % of the liquid effluent.

An alternate embodiment of the present invention is a process for disproportionation of toluene to benzene and xylene that includes passing a toluene/hydrogen feedstock over a niobium-mordenite catalyst at reaction conditions sufficient to provide toluene conversion at a rate of at least 30 percent and provide non-aromatic selectivity of less than 1.0 wt %. The niobium content of the catalyst can be between 0.005 wt % to 3.0 wt %.

In one embodiment the toluene disproportionation reaction process can continue with a toluene conversion of at least 30 percent for at least 30 days with an average catalyst deactivation no more than 1.0° C./day. In an alternate embodiment the toluene disproportionation reaction process can continue with a toluene conversion of at least 40 percent for at least 30 days with an average catalyst deactivation no more than 0.5° C./day. The reaction temperature can be adjusted to maintain the toluene conversion level of at least 40 percent. The methylcyclopentane content can be less than 0.005 wt % of the liquid effluent.

In yet another embodiment of the present invention a process for disproportionation of toluene to benzene and xylene includes passing a toluene/hydrogen feedstock over a niobium-mordenite catalyst with a niobium content of the catalyst is at least 0.05 wt %. The reaction conditions are sufficient to provide toluene conversion at a rate of at least 30 percent and include a reaction temperature between 150° C. and 471° C. (300° F.-880° F.) and reaction pressure between 200 psig to 800 psig. The non-aromatic selectivity is less than 0.75 wt % and the process is capable of such conversion for at least 30 days with an average catalyst deactivation no more than 1.0° C./day.

DETAILED DESCRIPTION

The use of Ni/Mordenite molecular sieve catalysts in toluene disproportionation and heavy aromatic conversion reactions is well known in the art. The present invention provides an improved means of conducting these reactions wherein the nonaromatic selectivity is comparable or lower than the currently used Ni/Mordenite catalyst, even without sulfiding.

In accordance with the present invention, there is provided a novel process for the disproportionation of toluene over a metal promoted molecular sieve catalyst in which a Niobium-modified Mordenite catalyst is used, resulting in low amounts of nonaromatics.

One embodiment of the present invention is a molecular sieve catalyst containing niobium useful in the conversion of hydrocarbons. In an embodiment the molecular sieve catalyst contains at least 0.005 wt % niobium. In alternate embodiments the molecular sieve catalyst contains at least 0.05 wt % niobium or at least 0.5 wt % niobium. The molecular sieve catalyst can be a zeolite, and can be a mordenite zeolite. The catalyst can be used in a toluene disproportionation reaction process and can provide a toluene conversion at a rate of at least 30 wt % and non-aromatic selectivity of less than 1.0 wt %, or in an alternate embodiment at least 40 wt % and non-aromatic selectivity of less than 0.5 wt %. The toluene disproportionation reaction process can continue with a toluene conversion of at least 30 percent for at least 30 days with an average catalyst deactivation no more than 1.0° C./day, or in an alternate embodiment a toluene conversion of at least 40 percent for at least 30 days with an average catalyst deactivation no more than 0.5° C./day. The toluene disproportionation reaction process can provide a toluene conversion rate of at least 30 wt % and a methylcyclopentane content of less than 0.005 wt % of the liquid effluent.

An alternate embodiment of the present invention is a process for disproportionation of toluene to benzene and xylene that includes passing a toluene/hydrogen feedstock over a niobium-mordenite catalyst at reaction conditions sufficient to provide toluene conversion at a rate of at least 30 percent and provide non-aromatic selectivity of less than 1.0 wt %. The niobium content of the catalyst can be between 0.005 wt % to 3.0 wt %. In an embodiment of the invention the toluene conversion is at least 40 percent. The non-aromatic selectivity can be less than 0.5 wt %. The methylcyclopentane content of the liquid effluent can be less than 0.005 wt %.

In one embodiment the toluene disproportionation reaction process can continue with a toluene conversion of at least 30 percent for at least 30 days with an average catalyst deactivation no more than 1.0° C./day. In an alternate embodiment the toluene disproportionation reaction process can continue with a toluene conversion of at least 40 percent for at least 30 days with an average catalyst deactivation no more than 0.5° C./day. The reaction temperature can be adjusted to maintain the toluene conversion level of at least 40 percent.

The reaction temperature can range from 150° C.-471° C. (300° F.-880° F.). The hydrogen:toluene molar ratio can be between 0.05:1 to 4:1. The reaction pressure can range between 200 psig to 800 psig.

In yet another embodiment of the present invention a process for disproportionation of toluene to benzene and xylene includes passing a toluene/hydrogen feedstock over a niobium-mordenite catalyst with a niobium content of the catalyst is at least 0.05 wt %. The reaction conditions are sufficient to provide toluene conversion at a rate of at least 30 percent and include a reaction temperature between 150° C. and 471° C. (300° F.-880° F.) and reaction pressure between 200 psig to 800 psig. The non-aromatic selectivity is less than 0.75 wt % and the process is capable of such conversion for at least 30 days with an average catalyst deactivation no more than 1.0° C./day.

EXAMPLE

In one experiment a Zeolyst Mordenite Extrudate CPX51, from Zeolyst International of Valley Forge, Pa., USA, was used as the base material and was impregnated with 1.914 wt % Niobium using a wetness incipient method according to the following procedure:

1. The catalyst was dried at 110° C. over night. Its void volume was then measured by filling with deionized water and was calculated as 0.45 ml/g.
2. 3.2703 grams of $NbCl_5$ salt was dissolved in 33.8 ml to make an aqueous solution.
3. The Nb solution was impregnated to the dried catalyst by insipient wetness method.
4. The impregnated catalyst was dried at between 20° C. to 30° C., then dried further at 110° C. Later it was calcined at 550° C. for 2 hrs. The dried catalyst was measured to have 1.914 wt % Niobium content.

The impregnated catalyst was evaluated in a lab scale reactor for disproportionation of toluene to benzene and xylene. The testing conditions are summarized as following.

| | |
|---|---|
| Reactor - down flow | Niobium - Mordenite catalyst prepared in-house Nb 1.9 wt % |
| Feed | Toluene |
| LHSV | 3/hr |
| H2/HC molar ratio | 1:1 then 3:1 when NA are below 1%. |
| Temperature | Adjusted to hold constant conversion |
| RX Inlet Pressure | 600 psig |
| Target conversion | 47 ± 1% (53% toluene in effluent) |
| Catalyst volume | 30 ml, 14-20 mesh without dilution |

The reactor was flushed with flowing nitrogen for 15 minutes and pressure checked. It was switched to hydrogen flow at 1 L/min and the pressure increased to 600 psig. The temperature was ramped at 50° C./h to 200° C. (392° F.) and held overnight. The following morning it was ramped at a rate of 50° C./hr to 250° C. (485° F.) and held for two hours. The hydrogen flow was decreased from 1 L/min to a 1:1 hydrogen to hydrocarbon ratio. The temperature was ramped at 6° C./h to 350° C. (662° F.) after the feed was switched to toluene. Then the temperature was adjusted slowly during the following 2-3 days to achieve 47% conversion of toluene (about 360° C. or 680° F.). After the nonaromatics content in the product fell below 1%, the hydrogen ratio to hydrocarbon was increased to 3:1. The first sample showed very low liquid nonaromatics, at 0.5% on day 1 and then below 0.4% even without sulfiding during startup. Therefore the hydrogen rate was increased to 3:1 hydrogen to hydrocarbon ratio.

Figure 1:
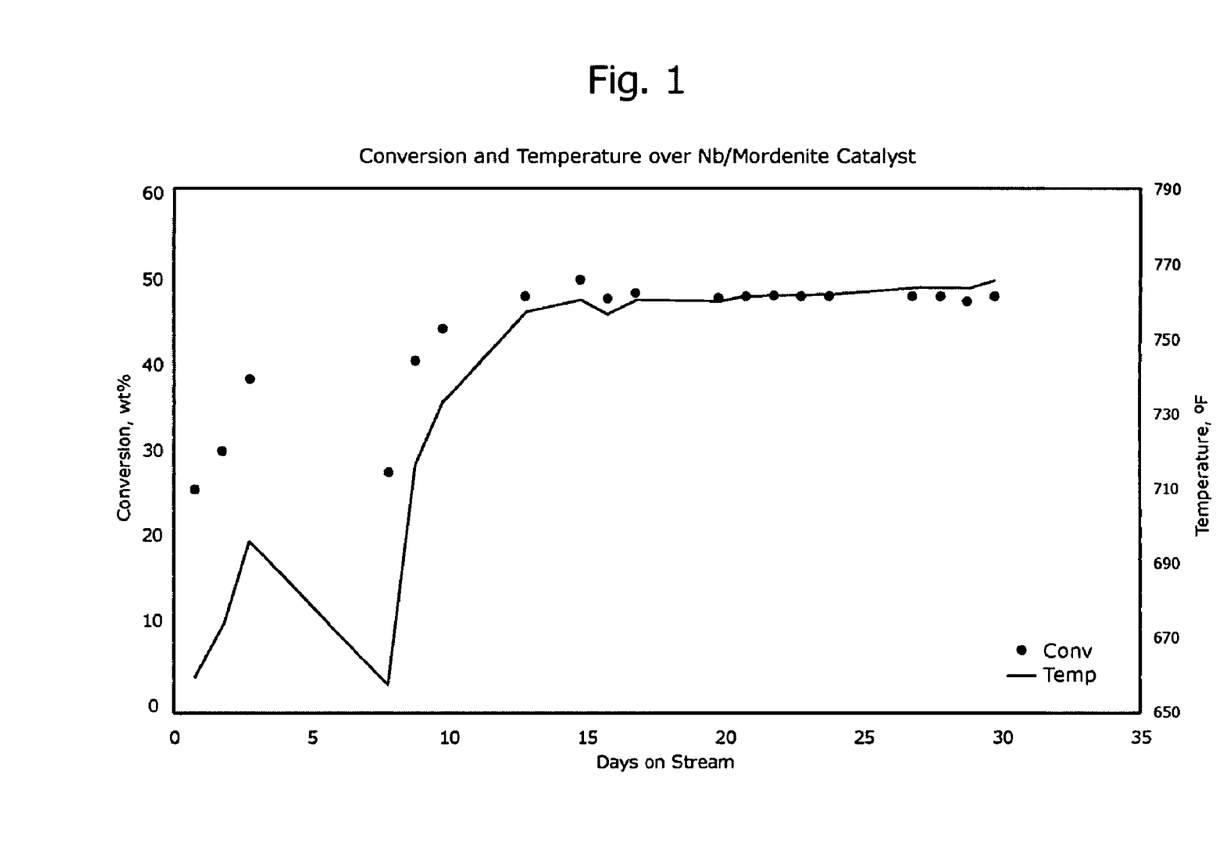
FIG. 1 is a graph of toluene conversion and bed temperature for a TDP reaction using a Nb/Mordenite catalyst.

FIG. 1 shows the toluene conversion and bed temperature during the study of the disproportionation of toluene to benzene and xylene using the Nb-Mordenite catalyst. The bed temperature decreased for a few days early in the study due to an unplanned shutdown. At Day 13 after a stabilization period the conversion maintained at approximately 47% with minor temperature adjustments and the deactivation rate (temperature rise) was approximately 0.37° F./day (0.21° C./day) with an average bed temperature of 760° F. (404° C.).

Figure 2:
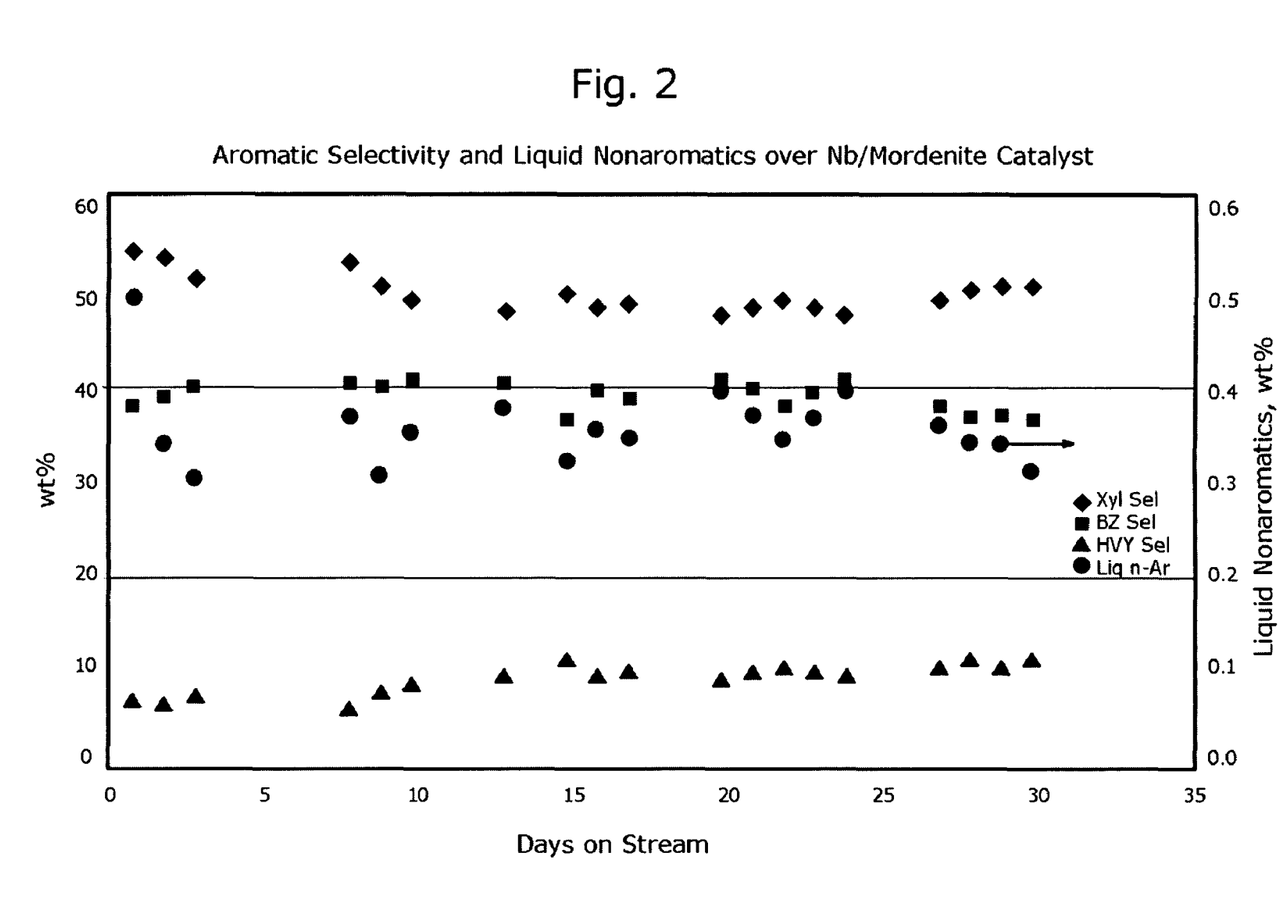
FIG. 2 is a graph of the aromatic and liquid nonaromatic selectivity from the TDP reaction using a Nb/Mordenite catalyst without sulfiding.

FIG. 2 shows the aromatic selectivity for the aromatic products of benzene, xylene and heavy aromatics, along with liquid nonaromatics from the study. The liquid nonaromatics were very low at 0.5% on day 1, and then below 0.4% throughout the study, even without sulfiding during startup. The aromatic selectivity's were within expected ranges, on average 38.8% for benzene, 49.1% for xylenes and 10.4% for heavies.

Figure 3:
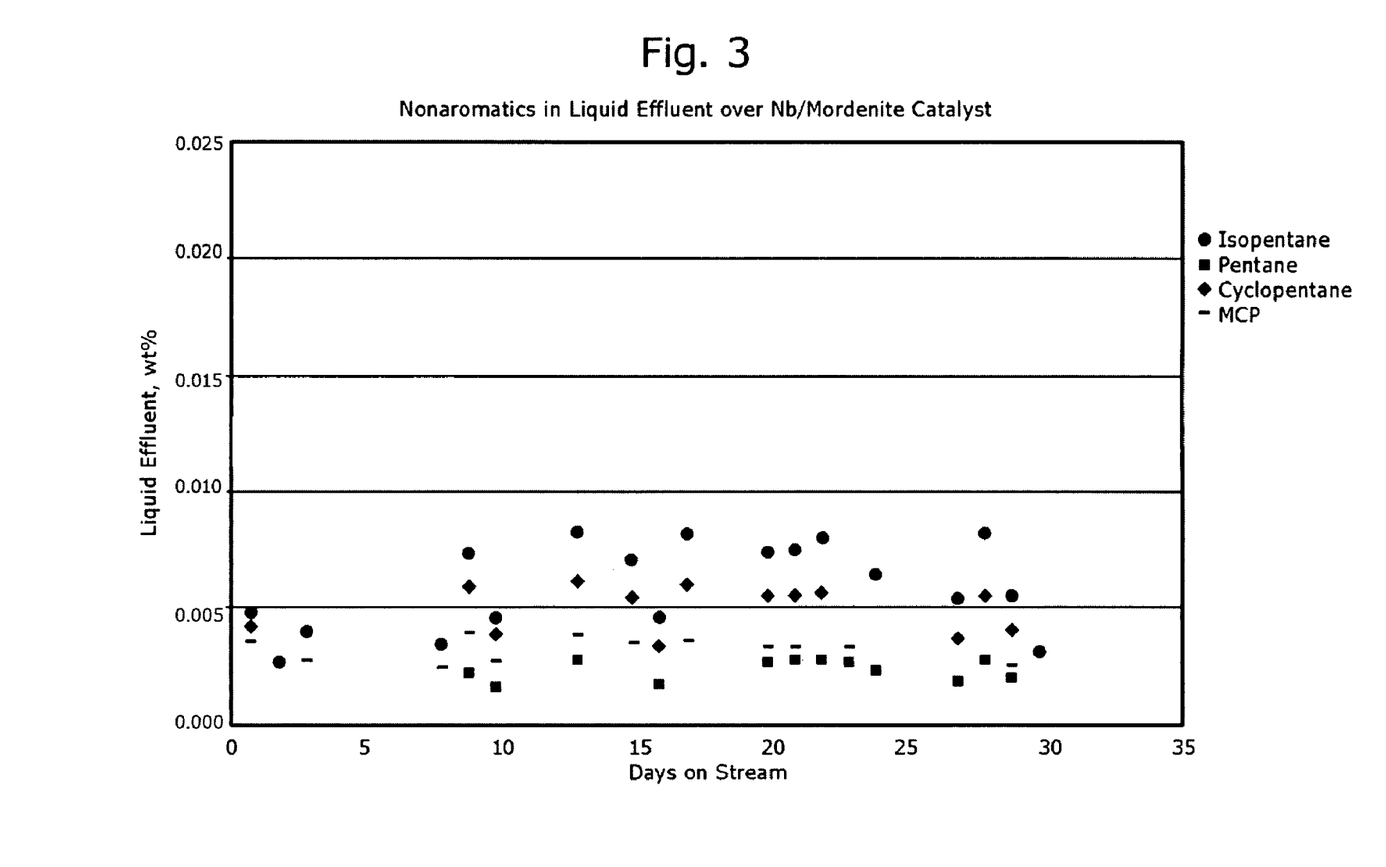
FIG. 3 graphically shows the breakdown of C5+ nonaromatics obtained from the TDP reaction using a Nb/Mordenite catalyst.

FIG. 3 shows the breakdown of the C5+ nonaromatic product. The methylcyclopentane (MCP) content is less than 0.004 wt % of the liquid effluent, which is lower than the Ni/Mordenite catalysts that have been tested, as can be seen in Table 4. MCP has essentially the same boiling point as benzene, making it difficult to isolate and remove. There is a desire to minimize the creation of MCP for this reason. The major constituents of the C5+ nonaromatic product are each less than 0.010 wt % of the liquid effluent, and include isopentane, pentane, cyclopentane and others as shown.

Figure 4:
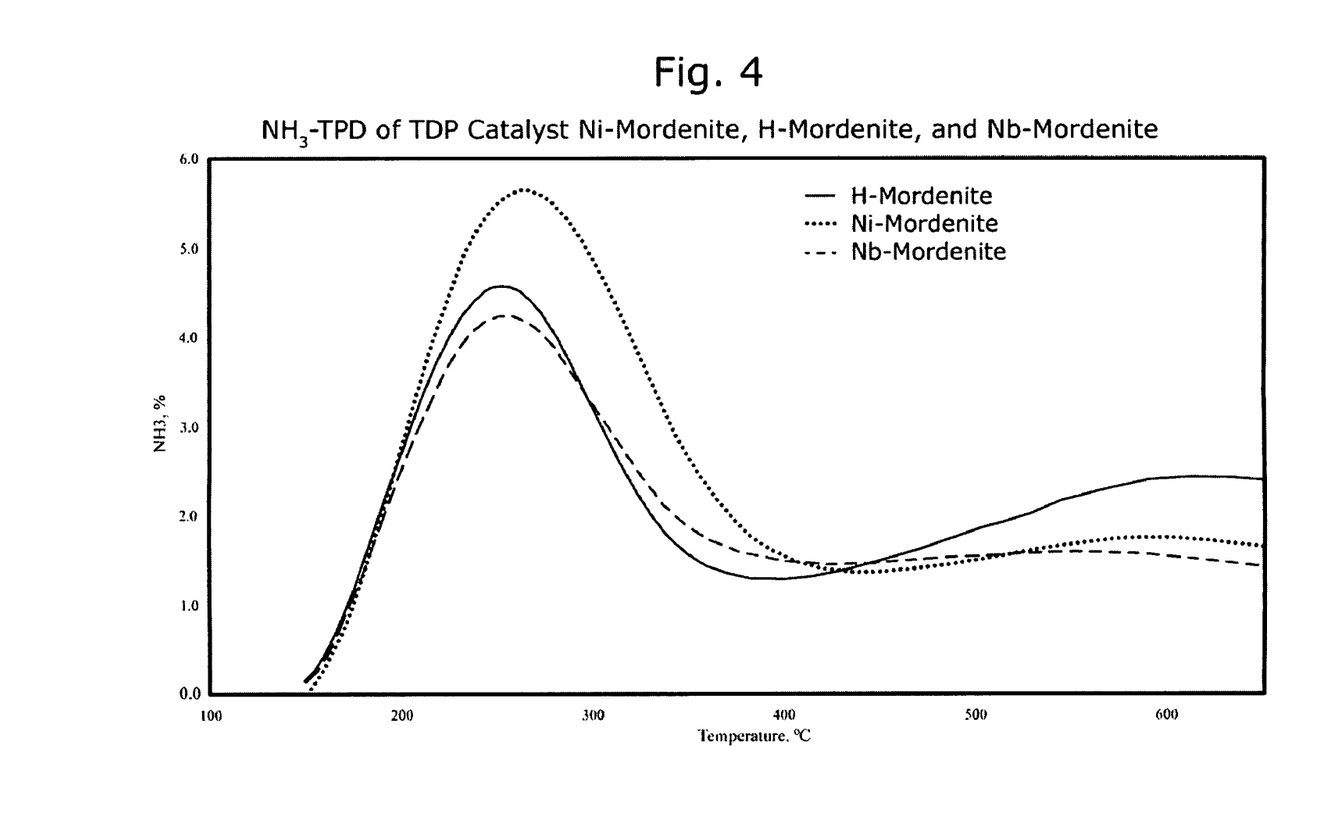
FIG. 4 graphically shows a comparison of results between the in-house prepared Nb/Mordenite catalyst, a commercial H-Mordenite, and a commercial Ni/Mordenite when tested using an ammonium temperature programmed desorption ($NH_3$-TDP) procedure.

FIG. 4 is a NH3-TDP graph (ammonium temperature programmed desorption) comparison between the in-house prepared Nb/Mordenite catalyst of the present invention and two commercial catalysts, an H-Mordenite (Zeolyst CP-X51) and Ni/Mordenite (Zeolyst CP-751). The acidity of Nb/Mordenite is slightly lower than the H-Mordenite catalyst and is substantially lower than the Ni/Mordenite catalyst. The lower acidity indicates fewer active acid sites and is thought to be why the Nb/Mordenite catalyst required a much higher bed temperature (~90+° F., ~50+° C.) for the TDP reaction.

The Nb/Mordenite showed high activity and stability for TDP conversion with low nonaromatic production. In this particular study the activity was stable around 760° F. (404° C.). The quantity of nonaromatic compounds in the product with the Nb/Mordenite catalyst without sulfiding was comparable with results from the Ni/Mordenite type TDP catalyst with sulfiding. Elimination of the need for sulfiding can reduce cost and may enable shorter start-up times and achieve on-spec products in a shorter amount of time after start-up.

Figure 5:
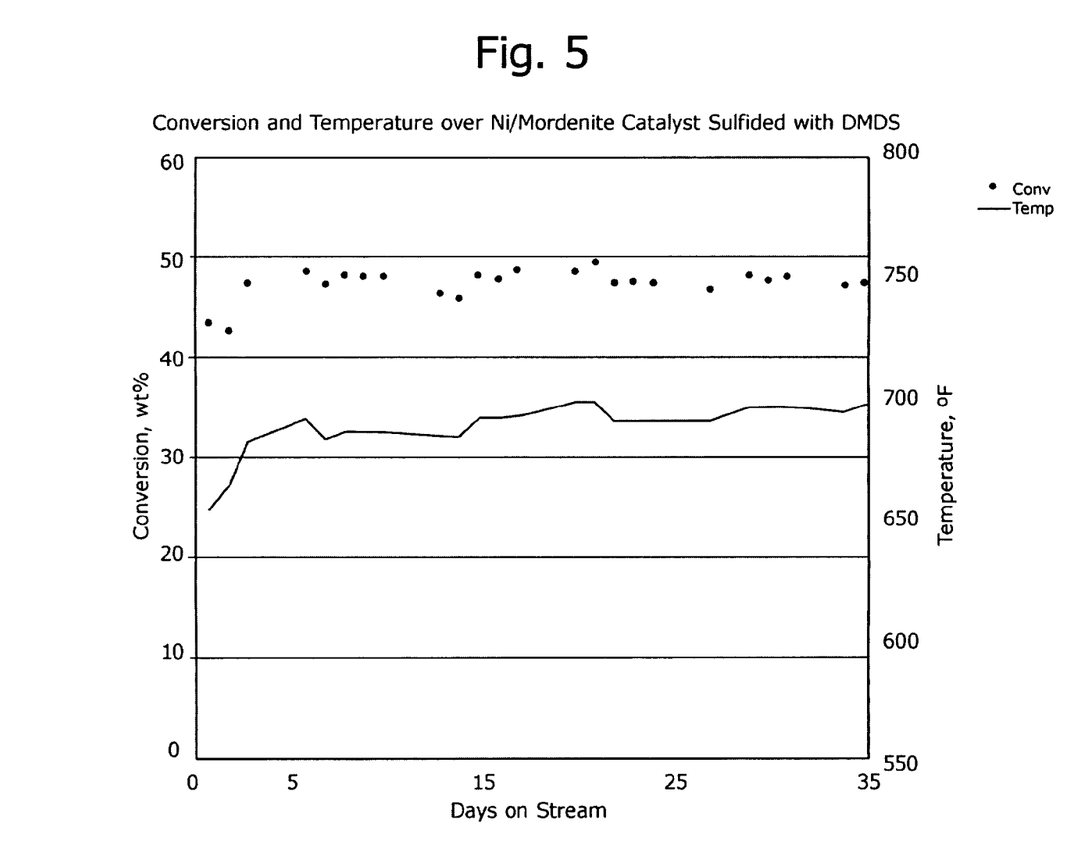
FIG. 5 is a graph of toluene conversion and bed temperature for a TDP reaction using a commercial Ni/Mordenite catalyst with sulfiding.

The following Table 1 and 2 give experimental data from the Experiment for the disproportionation of toluene to benzene and xylene using the Nb-Mordenite catalyst. All values are in wt % unless noted otherwise. This data is shown graphically in FIGS. 1-3. Table 3 gives comparative data from the disproportionation of toluene to benzene and xylene using a commercial 1% Ni/Mordenite catalyst (Zeolyst CP-751). The comparative data is graphed in FIG. 5.

TABLE 1

Toluene Conversion, Temp, Aromatic Selectivity and Liquid Nonaromatics over Nb/Mordenite Catalyst

| Day | Toluene conversion | Temp ° F. | Xylene Selectivity | Benzene Selectivity | Heavies Selectivity | Liquid non-aromatic Selectivity |
|---|---|---|---|---|---|---|
| 1 | 25.6 | 660 | 54.1 | 38.1 | 7.1 | 0.50 |
| 2 | 30.1 | 674 | 53.8 | 39.2 | 6.6 | 0.34 |
| 3 | 38.4 | 697 | 51.7 | 40.3 | 7.6 | 0.30 |
| 8 | 27.6 | 658 | 53.2 | 40.3 | 5.9 | 0.37 |
| 9 | 40.3 | 716 | 50.7 | 40.1 | 8.0 | 0.31 |
| 10 | 44.0 | 733 | 49.2 | 40.9 | 8.7 | 0.35 |
| 13 | 47.7 | 757 | 48.1 | 40.4 | 9.9 | 0.38 |
| 15 | 49.6 | 761 | 50.0 | 36.7 | 11.6 | 0.32 |

TABLE 1-continued

Toluene Conversion, Temp, Aromatic Selectivity and Liquid Nonaromatics over Nb/Mordenite Catalyst

| Day | Toluene conversion | Temp ° F. | Xylene Selectivity | Benzene Selectivity | Heavies Selectivity | Liquid non-aromatic Selectivity |
|---|---|---|---|---|---|---|
| 16 | 47.5 | 757 | 48.6 | 39.8 | 10.0 | 0.36 |
| 17 | 48.1 | 760 | 48.8 | 39.0 | 10.3 | 0.35 |
| 20 | 47.5 | 760 | 47.8 | 40.9 | 9.5 | 0.40 |
| 21 | 47.7 | 762 | 48.4 | 39.9 | 10.0 | 0.37 |
| 22 | 47.8 | 762 | 49.3 | 38.1 | 10.5 | 0.35 |
| 23 | 47.7 | 762 | 48.7 | 39.6 | 9.9 | 0.37 |
| 24 | 47.6 | 762 | 47.8 | 40.9 | 9.5 | 0.40 |
| 27 | 47.7 | 764 | 49.5 | 38.2 | 10.7 | 0.36 |
| 28 | 47.7 | 764 | 50.3 | 36.9 | 11.0 | 0.34 |
| 29 | 47.1 | 764 | 50.5 | 37.2 | 10.9 | 0.34 |
| 30 | 47.8 | 766 | 50.7 | 36.5 | 11.3 | 0.31 |

TABLE 2

C5+ Nonaromatics in Liquid Effluent over Nb/Mordenite Catalyst

| Day | Isopentane | Pentane | Cyclopentane | MCP |
|---|---|---|---|---|
| 1 | 0.0048 | 0.0000 | 0.0043 | 0.0036 |
| 2 | 0.0028 | 0.0000 | 0.0000 | 0.0000 |
| 3 | 0.0040 | 0.0000 | 0.0000 | 0.0028 |
| 8 | 0.0035 | 0.0000 | 0.0000 | 0.0025 |
| 9 | 0.0074 | 0.0022 | 0.0060 | 0.0040 |
| 10 | 0.0046 | 0.0016 | 0.0039 | 0.0027 |
| 13 | 0.0083 | 0.0028 | 0.0061 | 0.0039 |
| 15 | 0.0071 | 0.0000 | 0.0055 | 0.0035 |
| 16 | 0.0047 | 0.0017 | 0.0034 | 0.0000 |
| 17 | 0.0082 | 0.0000 | 0.0060 | 0.0036 |
| 20 | 0.0075 | 0.0027 | 0.0055 | 0.0034 |
| 21 | 0.0076 | 0.0028 | 0.0055 | 0.0033 |
| 22 | 0.0081 | 0.0028 | 0.0057 | 0.0000 |
| 23 | 0.0000 | 0.0027 | 0.0000 | 0.0033 |
| 24 | 0.0065 | 0.0024 | 0.0000 | 0.0000 |
| 27 | 0.0055 | 0.0018 | 0.0036 | 0.0000 |
| 28 | 0.0082 | 0.0028 | 0.0056 | 0.0000 |
| 29 | 0.0056 | 0.0020 | 0.0041 | 0.0025 |
| 30 | 0.0032 | 0.0000 | 0.0000 | 0.0000 |

Comparative data for disproportionation of toluene to benzene and xylene using a commercial Ni/Mordenite catalyst, Zeolyst CP 751.

TABLE 3

Toluene Disproportionation Data using Ni/Mordenite with Sulfiding

| Day | Toluene conversion | Temp ° F. | Xylene Selectivity | Benzene Selectivity | Heavies Selectivity | Liquid non-aromatic Selectivity |
|---|---|---|---|---|---|---|
| 1 | 43.5 | 653 | 47.6 | 42.4 | 8.6 | 0.77 |
| 2 | 42.7 | 663 | 47.7 | 42.4 | 8.5 | 0.63 |
| 3 | 47.4 | 682 | 47.6 | 40.5 | 10.4 | 0.49 |
| 6 | 48.5 | 692 | 47.7 | 40.2 | 10.6 | 0.53 |
| 7 | 47.3 | 683 | 48.5 | 40.6 | 9.6 | 0.39 |
| 8 | 48.1 | 686 | 48.9 | 39.7 | 10.1 | 0.38 |
| 9 | 48.1 | 686 | 47.9 | 40.6 | 9.6 | 0.39 |
| 10 | 48.1 | 686 | 48.2 | 40.3 | 9.7 | 0.37 |
| 13 | 46.5 | 684 | 50.2 | 38.5 | 10.1 | 0.32 |
| 14 | 45.9 | 684 | 49.1 | 40.2 | 9.6 | 0.36 |
| 15 | 48.2 | 692 | 48.6 | 40.0 | 9.9 | 0.37 |
| 16 | 47.8 | 692 | 49.0 | 39.7 | 9.9 | 0.36 |
| 17 | 48.7 | 693 | 49.3 | 39.1 | 10.2 | 0.36 |
| 20 | 48.6 | 698 | 47.8 | 38.1 | 10.3 | 0.36 |
| 21 | 49.3 | 698 | 48.3 | 40.4 | 10.0 | 0.38 |
| 22 | 47.4 | 690 | 49.3 | 39.4 | 10.0 | 0.36 |

TABLE 3-continued

Toluene Disproportionation Data using Ni/Mordenite with Sulfiding

| Day | Toluene conversion | Temp °F. | Xylene Selectivity | Benzene Selectivity | Heavies Selectivity | Liquid non-aromatic Selectivity |
|---|---|---|---|---|---|---|
| 23 | 47.4 | 691 | 49.6 | 38.8 | 10.2 | 0.34 |
| 24 | 47.3 | 690 | 49.5 | 39.2 | 10.0 | 0.36 |
| 27 | 46.7 | 690 | 49.2 | 39.8 | 9.7 | 0.36 |
| 29 | 48.1 | 696 | 49.2 | 39.1 | 10.3 | 0.34 |
| 30 | 47.7 | 696 | 48.7 | 40.2 | 10.0 | 0.37 |
| 31 | 48.1 | 696 | 49.9 | 38.1 | 10.6 | 0.35 |
| 34 | 47.0 | 694 | 50.0 | 38.5 | 10.1 | 0.33 |
| 35 | 47.3 | 697 | 48.8 | 39.4 | 9.9 | 0.36 |

TABLE 4

C5+ Nonaromatics in Liquid Effluent over Ni/Mordenite Catalyst.

| Day | Isopentane | Pentane | Cyclopentane | MCP |
|---|---|---|---|---|
| 1 | 0.0187 | 0.0052 | 0.0191 | 0.0196 |
| 2 | 0.0174 | 0.0043 | 0.0153 | 0.0123 |
| 3 | 0.0061 | 0.0016 | 0.0052 | 0.0043 |
| 6 | 0.0024 | 0.0000 | 0.0000 | 0.0000 |
| 7 | 0.0049 | 0.0000 | 0.0000 | 0.0000 |
| 8 | 0.0029 | 0.0000 | 0.0000 | 0.0000 |
| 9 | 0.0086 | 0.0026 | 0.0000 | 0.0055 |
| 10 | 0.0066 | 0.0019 | 0.0056 | 0.0044 |
| 13 | 0.0065 | 0.0019 | 0.0055 | 0.0045 |
| 14 | 0.0106 | 0.0028 | 0.0000 | 0.0063 |
| 15 | 0.0101 | 0.0027 | 0.0074 | 0.0056 |
| 16 | 0.0083 | 0.0024 | 0.0000 | 0.0051 |
| 17 | 0.0072 | 0.0022 | 0.0000 | 0.0046 |
| 20 | 0.0100 | 0.0030 | 0.0000 | 0.0057 |
| 21 | 0.0109 | 0.0032 | 0.0000 | 0.0061 |
| 22 | 0.0082 | 0.0000 | 0.0062 | 0.0049 |
| 23 | 0.0077 | 0.0000 | 0.0061 | 0.0047 |
| 24 | 0.0094 | 0.0000 | 0.0078 | 0.0059 |
| 27 | 0.0078 | 0.0000 | 0.0065 | 0.0049 |
| 29 | 0.0090 | 0.0000 | 0.0075 | 0.0055 |
| 30 | 0.0100 | 0.0031 | 0.0082 | 0.0060 |
| 31 | 0.0065 | 0.0020 | 0.0054 | 0.0042 |
| 34 | 0.0049 | 0.0015 | 0.0000 | 0.0032 |
| 35 | 0.0101 | 0.0031 | 0.0000 | 0.0059 |

Various terms are used herein, to the extent a term used in not defined herein, it should be given the broadest definition persons in the pertinent art have given that term as reflected in printed publications and issued patents.

The term "activity" refers to the weight of product produced per weight of the catalyst used in a process per hour of reaction at a standard set of conditions (e.g., grams product/gram catalyst/hr).

The term "deactivated catalyst" refers to a catalyst that has lost enough catalyst activity to no longer be efficient in a specified process. Such efficiency is determined by individual process parameters.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples.

While the foregoing is directed to embodiments of the present invention, other and further embodiments of the invention may be devised without departing from the basic scope thereof and the scope thereof is determined by the claims that follow.

What is claimed is:

1. A process for disproportionation of toluene to benzene and xylene, comprising:
    passing a toluene/hydrogen feedstock over a niobium-mordenite zeolite catalyst consisting of niobium and mordenite at reaction conditions sufficient to provide toluene conversion at a rate of at least 30 percent and provide non-aromatic selectivity of less than 0.75 wt %;
    wherein the niobium-mordenite catalyst is prepared by subjecting a mordenite extrudate to a solution comprising niobium by incipient wetness impregnation.

2. The process of claim 1, wherein the niobium content of the catalyst is between 0.005 wt % to 3.0 wt %.

3. The process of claim 1, wherein the niobium content of the catalyst is at least 0.05 wt %.

4. The process of claim 1, wherein the toluene conversion is at least 40 percent.

5. The process of claim 1, wherein the reaction temperature ranges from 150° C.-471° C. (300° F.-880° F.).

6. The process of claim 1, wherein the non-aromatic selectivity of less than 0.5 wt %.

7. The process of claim 1, wherein the toluene conversion is at least 30 wt % and the methylcyclopentane content is less than 0.005 wt % of the liquid effluent.

8. The process of claim 1, wherein the toluene disproportionation reaction process can continue with a toluene conversion of at least 30 percent for at least 30 days with an average catalyst deactivation no more than 1.0° C./day.

9. The process of claim 1, wherein the toluene disproportionation reaction process can continue with a toluene conversion of at least 40 percent for at least 30 days with an average catalyst deactivation no more than 0.5° C./day.

10. The process of claim 1, wherein the reaction temperature is adjusted to maintain the toluene conversion level of at least 40 percent.

11. The process of claim 1, wherein the hydrogen:toluene molar ratio is between 0.05:1 to 4:1.

12. The process of claim 1, wherein the reaction pressure range is between 200 psig to 800 psig.

13. A process for disproportionation of toluene to benzene and xylene, comprising:
    passing a toluene/hydrogen feedstock over a niobium-mordenite catalyst at reaction conditions sufficient to provide toluene conversion at a rate of at least 30 percent;
    the niobium content of the catalyst is at least 0.05 wt %;
    the reaction temperature is between 150° C. and 471° C. (300° F.-880° F.);

the reaction pressure is between 200 psig to 800 psig;
the non-aromatic selectivity is less than 0.75 wt %; and
the process is capable of such conversion for at least 30 days with an average catalyst deactivation no more than 1.0° C./day;
wherein the niobium-mordenite catalyst is prepared by extrudate to a solution comprising niobium by incipient wetness impregnation;
wherein the niobium-mordenite catalyst consists of niobium and mordenite.

14. The process of claim 1, wherein the niobium-mordenite catalyst has a lower acidity than hydrogen-mordenite and nickel-mordenite.

\* \* \* \* \*